United States Patent [19]

Robertson

[11] 4,321,213

[45] Mar. 23, 1982

[54] 2,4,4'-TRIMETHYLPENTYL, CYCLOHEXYLPHOSPHINIC ACID AND ITS PREPARATION

[75] Inventor: Allan J. Robertson, Niagara, Canada

[73] Assignee: Cyanamid Canada, Inc., Willowdale, Canada

[21] Appl. No.: 263,459

[22] Filed: May 14, 1981

[51] Int. Cl.$^3$ .............................................. C07F 9/30
[52] U.S. Cl. ........................... 260/502.4 R; 75/119; 210/634; 210/912; 423/139
[58] Field of Search ................................... 260/502.4 R

[56] References Cited

U.S. PATENT DOCUMENTS

| | | | |
|---|---|---|---|
| 2,724,718 | 11/1955 | Stiles et al. | 260/502.4 R |
| 2,957,931 | 10/1960 | Hamilton et al. | 260/502.4 R |
| 3,052,514 | 9/1962 | Schmitt | 260/502.4 R |
| 3,322,716 | 5/1967 | Klein et al. | 260/502.4 R |
| 3,966,569 | 6/1976 | Reinhardt et al. | 423/139 |

FOREIGN PATENT DOCUMENTS 673451  6/1952  United Kingdom ......... 260/502.4 R

*Primary Examiner*—Joseph E. Evans
*Attorney, Agent, or Firm*—Paul W. Leuzzi, II

[57] ABSTRACT

Free Radical Addition of Mono 2,4,4'-trimethylpentylphosphine to cyclohexene followed by the oxidation of the 2,4,4'-trimethylpentyl, cyclohexylphosphine with two moles of hydrogen peroxide is employed to prepare 2,4,4'-trimethylpentyl, cyclohexylphosphinic acid. The 2,4,4'-trimethylpentyl, cyclohexylphosphinic acid is useful as a cobalt extractant.

1 Claim, No Drawings

2,4,4'-TRIMETHYLPENTYL, CYCLOHEXYLPHOSPHINIC ACID AND ITS PREPARATION

The invention relates to 2,4,4'-trimethylpentyl, cyclohexylphosphinic acid, i.e.,

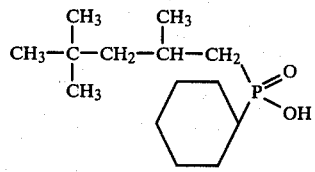

and a method for the production thereof which comprises free radical addition of mono 2,4,4'-trimethylpentylphosphine to cyclohexene followed by the oxidation of the 2,4,4'-trimethylpentyl, cyclohexylphosphine with two moles of hydrogen peroxide. The end product, either as an acid or in its salt form, finds utility as a cobalt extractant and, more specifically, as a selective extractant for cobalt (II) in aqueous cobalt (II)—bearing solutions containing nickel (II).

In the preparation of this compound free radical initiators of the azobis type are preferred although others, such as the peroxides, may be used. Azobisbutrylnitrile is the most preferred. The temperature range of the reaction is directly related to the half life of the initiator employed. For azobisbutrylnitrile the temperature range should be about 40°–110° C., preferably 60° to 90° C. The mole ratio of olefin to mono alkylphosphine can vary from 0.1 to 10 depending on the relative rates of formation of the di- and tri-alkylphosphines. Preferably the range is between 0.5 to 3.

In the oxidation stage, the oxidation of the dialkylphosphine to the dialkylphosphine oxide is exothermic and takes place readily at 30°–100°, preferably for this first oxidation step at 50°–70° C. To convert the dialkylphosphine oxide to the dialkylphosphine acid, the temperature should be increased to within 50° to 120° C., preferably 80° to 100° C. Higher temperatures tend to remove one alkyl group forming some monoalkylphosphonic acid. At lower temperatures the oxidation is rather slow and excessive reaction times may be required.

Whereas the exact scope of the instant invention is set forth in the appended claims, the following specific examples illustrate certain aspects of the present invention, and, more particularly, point out methods of evaluating the same. However, the examples are set forth for illustration only and are not to be construed as limitations on the present invention except as set forth in the appended claims. All parts and percentages are by weight unless otherwise specified.

EXAMPLE 1

500 Parts of 09.5% mono 2,4,4'trimethylpentylphosphine is charged along with 482 parts of cyclohexene to a 1 gallon autoclave. 15 parts of azobisobutrylnitrile (VAZO 64 ®) is added and the mixture quickly heated to 60° C. The temperature is then slowly raised from 60° C. to 87° C. over a 5½ hour period.

The product contained 39.36% cyclohexene, 22.70% mono 2,4,4' trimethylpentylphosphine, 35.26% 2,4,4' trimethylpentyl, cyclohexylphosphine, and 0.35% 2,4,4' trimethylpentyl, dicyclohexylphosphine.

A further 20 parts of azobisobutrylnitrile is added to the mixture. It is heated quickly to 60° C. and then slowly from 60° C. to 89° over a 6½ hour period.

The product contained 34.39% cyclohexene 11.14% mono 2,4,4'trimethylpentylphosphine, 48.3% 2,4,4' trimethylpentyl, cyclohexylphosphine, and 2.18% 2,4,4' trimethylpentyl dicyclohexylphosphine.

The product mixture is then distilled to remove the cyclohexene and mono 2,4,4'trimethylpentylphosphine. 516.9% of the residue containing 0.45% mono 2,4,4'trimethylpentylphosphine, 90.0% 2,4,4'trimethylpentyl cyclohexylphosphine and 3.48% 2,4,4' trimethylpentyl, dicyclohexylphosphine is placed in a stirred, heated resin flask under an inertr atmosphere. The mixture is heated to 50° C. and 575 mL of 24% $H_2O_2$ is added slowly with stirring over 1½ hours. During that time the temperature rose from 50° C. to 98° C. To completely oxidize all the dialkylphosphine to the phosphinic acid, an additional 500 g of 24% $H_2O_2$ is added and the mixture heated for a further 5 hours at 100° C.

The product is then decanted as a viscous oil. It assayed 85.97% phosphinic acid but also contained 9.58% mono 2,4,4' trimethylpentylphosphonic acid. During the severe oxidation conditions, a portion of the cyclohexyl groups were removed and the resulting 2,4,4' trimethylpentylphosphine is oxidized to 2,4,4' trimethylpentylphosphonic acid.

Most of the phosphonic acid is removed by scrubbing with 0.1 N NaOH and water. The final product assayed 85.37% 2,4,4' trimethylpentyl, cyclohexylphosphinic acid and 4.86% 2,4,4' trimethylpentylphosphonic acid.

The product is a viscous oil and had a pKa of 6.04 in 75% isopropanol. The $^{31}$P NMR chemical shift in toluene is $-53.13$ ppm with respect to 85% $H_3PO_4$.

EXAMPLE 2

The following example illustrates the ability of 2,4,4'-trimethylpentyl, cyclohexyl phosphinic acid to separate cobalt (II) from nickel (II).

The 2,4,4'-trimethylpentyl, cyclohexylphosphinic acid is dissolved in an aliphatic petroleum diluent (Solvesso ® 100) modified with 5% v/v isoderanol to obtain a concentration of 15% by volume, then a predetermined amount of 28% ammonium hydroxide is added to adjust the pH. An aliquot (50 mls) is shaken at 50° C. for 5 minutes at 50° C. with an equal volume of an aqueous solution containing 2.05 gpl of cobalt (II) and 102.4 gpl of nickel (II), respectively, as sulfate salts, to extract the cobalt (II) into the organic phase. The aqueous phase is then separated from the organic phase and analyzed for cobalt (II) content. Based on the results obtained, the percent cobalt (II) extracted is calculated by mass balance. The percent nickel (II) extracted is determined by analyzing the organic phase. The results obtained are shown in Table I.

TABLE I

| % Metal Extraction | | Co/Ni Separation | Equilibrium |
|---|---|---|---|
| Co | Ni | Factor | pH |
| 85.1 | 0.78 | 726 | 4.70 |
| 95.6 | 1.66 | 1274 | 5.18 |
| 98.4 | 3.19 | 1910 | 5.53 |
| 99.9 | 4.64 | 21030 | 5.80 |

(1) Separation Factor = $\dfrac{E_A° \text{ Co (II)}}{E_A° \text{ Ni (II)}}$, where $E_A° = \dfrac{\text{equilibrium concentration of the metal in the organic phase}}{\text{equilibrium concentration of the metal in the aqueous phase}}$

I claim:

1. The compound 2,4,4'-trimethylpentyl, cyclohexylphosphinic acid.

* * * * *